United States Patent [19]

Murray et al.

[11] Patent Number: 5,256,816

[45] Date of Patent: Oct. 26, 1993

[54] ENANTIOMERIC RESOLUTION

[75] Inventors: William T. Murray, Orangeburg; Robert E. Young, West Columbia; Azfar A. Choudhury; Deepak R. Patil, both of Orangeburg, all of S.C.

[73] Assignee: Ethyl Corporation, Richmond, Va.

[21] Appl. No.: 960,989

[22] Filed: Oct. 14, 1992

[51] Int. Cl.$^5$ .............................................. C07B 57/00
[52] U.S. Cl. ................................... 562/401; 558/414; 560/56; 560/57; 560/60; 560/100; 560/101; 560/105
[58] Field of Search ...................... 562/401; 558/414; 560/56, 57, 60, 100, 101, 105

[56] References Cited

U.S. PATENT DOCUMENTS

| | | | |
|---|---|---|---|
| 4,831,147 | 5/1989 | Russell | 546/302 |
| 4,865,770 | 9/1989 | Piselli | 562/402 |
| 4,910,309 | 3/1990 | Kershner et al. | 544/354 |
| 4,931,587 | 6/1990 | Piselli | 562/401 |
| 4,973,745 | 11/1990 | Blaschke et al. | 562/401 |

OTHER PUBLICATIONS

Collet et al., *Chem. Res.* 80(3), 215-230, (1980).
Jaques et al., *Enantiomers, Racemates and Resolutions*, Chapter 3, J. Wiley & Sons, New York, N.Y., (1981), pp. 167-213.
Collet, A., pp. 91-110, *Problems and Wonders of Chiral Molecules*, Simonyi, M. (Ed.), Akademiai Keado, Budapest (1990).

*Primary Examiner*—José G. Dees
*Assistant Examiner*—Vera C. Clarke
*Attorney, Agent, or Firm*—Hammond Richard J.

[57] ABSTRACT

A process for obtaining a substantially pure enantiomer of an aryl-substituted aliphatic carboxylic acid is described. In this process, the aryl-substituted aliphatic carboxylic acid is reacted with an inorganic base in the presence of an organic base to substantially enrich the precipitate in one of the enantiomers and an improved yield. Substantially pure, enantiomeric salt is separated, leaving a mother liquor comprising the solvent and aryl-substituted aliphatic carboxylic acid enriched in the other enantiomer.

11 Claims, No Drawings

ENANTIOMERIC RESOLUTION

FIELD OF THE INVENTION

This invention relates to a process for obtaining highly pure enantiomers of aryl-substituted carboxylic acids from a mixture of enantiomers.

BACKGROUND OF THE INVENTION

The resolution of racemates constitutes the main method for industrial preparation of pure enantiomers. Methods for such resolution include: direct preferential crystallization; crystallization of the diastereomeric salts and kinetic resolution. Pure enantiomers may also be produced by asymmetric synthesis (reaction of a chiral reagent or catalyst with a prochiral substrate).

Also referred to as resolution by entrainment, preferential crystallization is widely used on an industrial scale; for example, in the manufacture of α-methyl-L-dopa and chloramphenicol. It is technically feasible only with racemates which are so-called conglomerates. Unfortunately, less than 20 percent of all racemates are conglomerates. The rest are racemic compounds which cannot be separated by preferential crystallization.

If the racemate is not a conglomerate, a homogeneous solid phase of the two enantiomers co-exists in the same unit cell. These materials may be separated via diastereomer crystallization, which generally involves reaction of the racemate with an optically pure acid or base (the resolving agent) to form a mixture of diastereomeric salts which are then separated by crystallization. Ibuprofen, for example, is such a compound.

Diastereomer crystallization is widely used for the industrial synthesis of pure enantiomers. A typical example is the Andeno process for the manufacture of (D)-(−)-phenylglycine, an antibiotic intermediate, using optically pure camphor sulfonic acid as the resolving agent. Also see U.S. Pat. No. 4,752,417 for a diastereomeric procedure for resolving certain phenylacetic acid derivatives and U.S. Pat. No. 4,973,745 for resolving 2-arylpropionic acids.

The theoretical once-through yield of a resolution via diastereomer crystallization is 50 percent. However, in practice, a single recrystallization produces a composition that is simply enantiomerically enriched.

Another method for the resolution of racemates is kinetic resolution, the success of which depends on the fact that the two enantiomers react at different rates with a chiral addend.

Kinetic resolution can also be effected using chiral metal complexes as chemocatalysts, e.g., the enantioselective rhodium-BINAP-catalyzed isomerization of chiral allylic alcohols to the analogous prostaglandin intermediates reported by Noyori.

The enantioselective conversion of a prochiral substrate to an optically active product, by reaction with a chiral addend, is referred to as an asymmetric synthesis. From an economic viewpoint, the chiral addend functions in catalytic quantities. This may involve a simple chemocatalyst or a biocatalyst. An example of the former is the well-known Monsanto process for the manufacture of L-dopa by catalytic asymmetric hydrogenation. See Knowles, et al., *J. Am. Chem. Soc.*, 97, 2567 (1975). An example of the latter is the Genex process for the synthesis of L-phenylalanine by the addition of ammonia to transcinnamic acid in the presence of L-phenylalanine ammonia lyase (PAL). See Hamilton et al., *Trends in Biotechnology*, 3, 64–68, (1985). Also see Jacques et al., Enantiomers, Racemates and Resolutions, Chapter 3 (1981) incorporated herein by reference.

With the exception of the preferential crystallization process when applied to true conglomerates, the prior art processes typically produce a first mixture that is enantiomerically enriched. A number of crystallizations are required to obtain a substantially pure enantiomer.

OBJECTS OF THE INVENTION

It is an object of the present invention to provide a process for obtaining a substantially pure enantiomer of an aryl-substituted aliphatic carboxylic acid or the ester thereof.

It is a further object of the present invention to obtain such a substantially pure enantiomer from a composition of enantiomerically enriched or racemic aryl-substituted aliphatic carboxylic acid or the ester thereof.

PREFERRED EMBODIMENTS OF THE INVENTION

In the present specification, alkyl means straight or branched chain alkyl having 1 to 20 carbon atoms and includes, for example, methyl, ethyl, propyl, isopropyl, butyl, isobutyl, secondary butyl, tertiary butyl, pentyl, isopentyl, neopentyl, hexyl, heptyl, octyl, 2-ethylhexyl, 1,1,3,3-tetramethylbutyl, nonyl, decyl, dodecyl, tetradecyl, hexadecyl, octadecyl and eicosyl;

cycloalkyl means cyclic alkyl having 3 to 7 carbon atoms and includes cyclopropyl, cyclobutyl, cyclopentyl, cyclohexyl and cycloheptyl;

substituted phenyl or substituted naphthyl means phenyl or naphthyl substituted by at least one substituent selected from the group consisting of halogen (chlorine, bromine, fluorine or iodine), amino, nitro, hydroxy, alkyl, alkoxy which means straight or branched chain alkoxy having 1 to 10 carbon atoms, and includes, for example, methoxy, ethoxy, propoxy, isopropoxy, butoxy, isobutoxy, secondary butoxy, tertiary butoxy, pentyloxy, isopentyloxy, hexyloxy, heptyloxy, octyloxy, nonyloxy and decyloxy, haloalkyl which means straight or branched alkyl having 1 to 8 carbon atoms which is substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-dibromoethyl, 2,2-difluoroethyl, 3,3-dichloropropyl, 3,3-difluropropyl, 4,4-dichlorobutyl, 4,4-difluorobutyl, trichloromethyl, trifluoromethyl, 2,2,2-trifluoroethyl, 2,3,3-trifluoropropyl, 1,1,2,2-tetrafluoroethyl and 2,2,3,3-tetrafluoropropyl;

haloalkyl means straight or branched chain alkyl having 1 to 10 carbon atoms which is substituted at least one halogen as mentioned above;

hydroxyalkyl means that the alkyl moiety is straight or branched chain alkyl having 1 to 8 carbon atoms, and includes, for example, hydroxymethyl, 2-hydroxyethyl, 3-hydroxypropyl, 4-hydroxybutyl, 6-hydroxyhexyl, 8-hydroxyoctyl, 1-hydroxyethyl, 1-hydroxy-2-propyl, 2-hydroxypropyl, 2,3-dihydroxypropyl, 1,3-dihydroxy-2-propyl;

alkoxyalkyl means that the alkoxy moiety and the alkyl moiety each are straight or branched chain ones having 1 to 8 carbon atoms, and includes, for example, methoxymethyl, ethoxymethyl, propoxymethyl, isopropoxymethyl, butoxymethyl, isobutoxymethyl, tertiary butoxymethyl, pentyloxymethyl, hexyloxymethyl, heptyloxymethyl, octyloxymethyl, 2-methoxyethyl, 2-ethoxyethyl, 2-propoxyethyl, 2-butoxyethyl, 2-hexyloxyethyl, 2-octyloxyethyl, 3-methoxypropyl, 3-ethoxypropyl, 3-propoxypropyl, 3-butoxypropyl, 3-hexyloxypropyl, 3-octyloxypropyl, 4-methoxybutyl, 4-ethoxybutyl, 4-propoxybutyl, 4-hexyloxybutyl, 4-octyloxybutyl, 5-methoxypentyl, 5-ethoxypentyl, 5-propoxypentyl, 5-butoxypentyl, 5-pentyloxypentyl, 5-hexyloxypentyl, 5-octyloxypentyl, 6-methoxyhexyl, 6-ethoxyhexyl, 6-propoxyhexyl, 6-butoxyhexyl, 6-pentyloxyhexyl, 6-hexyloxyhexyl, 6-oxtyloxyhexyl, 8-methoxyoctyl, 8-ethoxyoctyl, 8-butoxyoctyl, 8-hexyloxyoctyl and 8-octyloxyoctyl;

acyloxyalkyl means that the acyl moiety is alkanoyl having 2 to 18 carbon atoms, benzoyl, substituted benzoyl, heteroarylcarbonyl or substituted heteroarylcarbonyl and the alkyl moiety is straight or branched chain alkyl having 1 to 8 carbon atoms, and includes, for example, acetoxymethyl, 2-acetoxyethyl, 3-acetoxypropyl, 4-acetoxybutyl, 6-acetoxyhexyl, 8-acetoxyoctyl, propionyloxymethyl, 2-propionyloxyethyl, 3-propionyloxypropyl, 4-propionyloxybutyl, 6-propionyloxyhexyl, 8-propionyloxyoctyl, isobutyryloxymethyl, 2-isobutyryloxyethyl, 4-isobutyryloxybutyl, pivaloyloxymethyl, 2-pivaloyloxyethyl, 4-pivaloyloxybutyl, butyryloxymethyl, 2-butyryloxyethyl, 4-butyryloxybutyl, valeryloxymethyl, 2-valeryloxyethyl, 4-valeryloxybutyl, hexanoyloxymethyl, 2-hexanoyloxyethyl, 4-hexanoyloxybutyl, octanoyloxymethyl, 2-octanoyloxyethyl, 4-octanoyloxybutyl, lauroyloxymethyl, 2-lauroyloxyethyl, 4-lauroyloxybutyl, stearoyloxymethyl, 2-stearoyloxyethyl, 4-stearoyloxybutyl, benzoyloxymethyl, 2-benzoyloxyethyl, 4-benzoyloxybutyl, furoyloxymethyl, 2-furoyloxyethyl, 4-furoyloxybutyl, thenoyloxymethyl, 2-thenoyloxyethyl, 4-thenoyloxybutyl, nicotinoyloxymethyl, 2-nicotinoyloxyethyl and 4-nicotinoyloxybutyl;

carboxyalkyl means that the alkyl moiety is straight or branched chain alkyl having 1 to 8 carbon atoms and includes, for example, carboxymethyl, 2-carboxymethyl, 3-carboxypropyl, 4- carboxybutyl, 6-carboxyhexyl and 8-carboxyoctyl;

alkoxycarbonylalkyl means that the alkoxy moiety and the alkyl moiety each are straight or branched chain ones having 1 to 8 carbon atoms, and includes, for example, methoxycarbonylmethyl, ethoxycarbonylmethyl, propoxycarbonylmethyl, isopropoxycarbonylmethyl, butoxycarbonylmethyl, isobutoxycarbonylmethyl, tertiary butoxycarbonylmethyl, pentlyoxycarbonylmethyl, hexyloxycarbonylmethyl, octyloxycarbonylmethyl, 2-methoxycarbonylethyl, 2-ethoxycarbonylethyl, 2-propoxycarbonylethyl, 2-butoxycarbonylethyl, 3-methoxycarbonylpropyl, 3-ethoxycarbonylpropyl, 3-propoxycarbonylpropyl, 3-butoxycarbonylpropyl, 4-methoxycarbonylbutyl, 4-ethoxycarbonylbutyl, 4-propoxycarbonylbutyl, 4-butoxycarbonylbutyl, 6-methoxycarbonylhexyl, 6-ethoxycarbonylhexyl, 8-methoxycarbonyloctyl and 8-ethoxycarbonyloctyl;

cyanoalkyl means that the alkyl moiety is straight or branched chain alkyl having 1 to 8 carbon atoms and includes, for example, cyanomethyl, 2-cyanoethyl, 3-cyanopropyl, 4-cyanobutyl, 6-cyanohexyl and 8-cyanooctyl.

The objective of the present invention is achieved by dissolving an enantiomerically enriched or racemic mixture of an aryl-substituted aliphatic carboxylic acid or the ester thereof in an inert solvent or a mixture of inert solvents. These materials have the following formula:

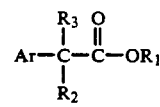

where $R_1$ is hydrogen or $C_1$ to $C_6$ linear or branched alkyl, $R_2$, and $R_3$ are hydrogen, alkyl, cycloalkyl, phenyl, substituted phenyl, naphthyl, substituted naphthyl, haloalkyl, hydroxyalkyl, alkoxyalkyl, acyloxyalkyl, carboxyalkyl, alkoxycarbonylalkyl or cyanoalkyl.

Ar is phenyl, substituted phenyl, naphthyl or substituted naphthyl.

Preferred compounds of Formula I are those of the formula:

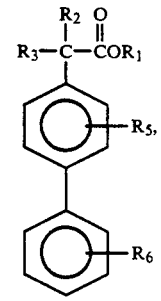

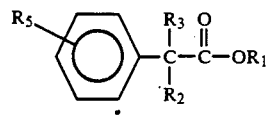

and

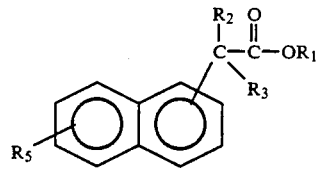

where $R_1$, and $R_2$ and $R_3$ are as previously defined and $R_5$ and $R_6$ are $C_1$ to $C_4$ linear or branched alkyl, $C_1$ to $C_4$ linear or branched alkoxy or halo.

The process of the present invention is particularly applicable to 2-(4-isobutylphenyl)propionic acid and especially in obtaining a preponderance of the d(+)isomer.

The invention is carried out by using a mixture of both the (+) and (−) (or dextro and levo rotatory forms) enantiomers of the carboxylic acids of formula I. However, it should be understood that the process itself does not convert one form of the stereoisomers to the other form but only separates such forms. Further in the preferred embodiment of this invention, the separation of enantiomers gives rise to a soluble product and an insoluble product which is enriched in one of the enantiomers. As such, a high purity product is obtained that requires a minimum number of recrystallizations (usually not more than two) to give a product with exceptionally high optical purity.

The process for the separation of the enantiomers used in the present invention is to form a salt of the aliphatic carboxylic acid of formula I with an inorganic base in an inert solvent. It is preferred that the inorganic base is a metal or a metallic or ammonium hydroxide, carbonate, bicarbonate or chloride. The metal may be any metal. Metals in Group I or II of the Periodic Table of Elements are preferred. Most preferably, the metal of the inorganic base is from Group IA. Especially preferred is sodium hydroxide.

It has been discovered that, in order to improve the recovery of one of the enantiomeric salts of the carboxylic acids of formula I from the reaction solution, sufficient organic base must be present. (A precipitation-enhancing amount of organic base is required.) Thus, when the amount of inorganic base used to produce the enriched salt solution is from about 0.05 to about 0.95 mole per mole of aryl-substituted carboxylic acid, an amount of organic base that is the same or different than the amount of inorganic base is used. Preferably, the moles of inorganic base is from about 0.40 to about 0.60 mole per mole of enantiomerically enriched aryl-substituted aliphatic carboxylic acid, most preferably from about 0.45 to about 0.55 mole per mole.

The precipitated material is the crystalline salt of the aryl-substituted aliphatic carboxylic acid. For example, if sodium hydroxide is used as the base in reacting with a carboxylic acid such as 2-(4-isobutylphenyl)propionic acid, the precipitated product is 2-(4-isobutylphenyl)-propionic acid, sodium salt. The process of the present invention will not produce the precipitated product in any significant yield, i.e., greater than 30% of theoretical, if an organic base is not added to the reaction solution. Yields of the substantially enantiomerically pure salt of about 70 to 90% are possible by the process of the present invention.

The organic base is preferably an aliphatic, aromatic or mixed aliphatic and aromatic amine. The only criteria for such organic base is that it react with the carboxylic acid to form a noncrystalline, nonprecipitating product (an oil). Preferred organic bases are low molecular weight organic bases such as the $C_1$ to $C_6$ linear or branched alkyl, $C_6$ to $C_{10}$ aryl or mixed alkyl/aryl amines; e.g. triethylamine, phenyl diethylamine and the like.

As a second step in this reaction sequence, an inert solvent may be added. Thus, water, or various aliphatic hydrocarbon solvents, i.e., hexane, heptane, octane, etc., aromatic hydrocarbon solvents, i.e., benzene, toluene, xylene, and alcohol solvents, i.e., methanol, ethanol, 1-propyl alcohol, etc., organic bases as solvents, i.e., triethyl amine, tributyl amine, bidutyl amine, etc. are acceptable for such solvent. It should be noted that when water is used as a solvent, the product precipitating is the hydrated form of the aryl-substituted aliphatic carboxylic acid salt.

The reaction can be heated, e.g. to a temperature of about 0° C. to about 125° C., preferably about 45° C. to 60° C.

The solid crystalline enantiomerically enriched salt of the aryl-substituted aliphatic carboxylic acid is isolated (step ii) from the mother liquor by any conventional method (centrifugation, filtration, decantation, etc.) The liquid remaining, the mother liquor, can then be partially evaporated or cooled or treated in any conventional manner recover the residual aryl-substituted carboxylic acid.

As such, the process provides a method of obtaining highly pure enantiomeric salt of the aryl-substituted carboxylic acid in higher than previously obtained yields.

The following examples are for illustration only and are not intended as limiting the invention in any way.

EXAMPLES

Example 1

To a solution of 100.2 g (0.48 mol) ibuprofen [89.5% d(+)] in 150 g hexane was added 11.6 g NaOH (0.29 mol) and 10.4 g water (0.58 mol). The contents were heated to 56° C. and held for 1 hour. The reaction mixture was then cooled to 5° C. over 2 hours, and the product was isolated by vacuum filtration followed by hexane (2×100 g) washing of the cake. The isolated d-(+)-ibuprofen, sodium salt dihydrate (45.7 g, 61.0% on NaOH, 36.6% based on ibuprofen), had an optical purity of 99.1% d(+).

Example 2

To a solution of 100 g (0.48 mol) ibuprofen [89.6% d(+)] in 150 g hexane was added 9.7 g NaOH (0.29 mol), 4.3 g (0.24 mol) water and 24.5 g (0.24 mol) triethylamine. The contents were heated to 56° C. and held for 20 minutes. The pot was then cooled to 5° C. over 2.25 hours, and the product was isolated by filtration. The cake was then washed (2×100 mL hexane) and air dried to yield 59.4 g of product (92.5% based on NaOH, 46.3% based on ibuprofen) with an optical purity of 99.3% d(+).

Example 3

To a solution of 100 g (0.48 mol ) ibuprofen [89.6% d(+)] in 233 g hexane was added 9.7 g NaOH (0.24 mol), 4.3 g (0.24 mL) water and 24.5 g (0.24 mol) triethylamine. The solution was heated to 65° C. for 0.5 hour, cooled to 7° C. over 2 hours, filtered, and the cake washed with 2×100 g hexane. The product was then air dried, yielding 59.4 g (92.1% based on NaOH, 46.1% based on ibuprofen) of d-(+)-ibuprofen, sodium salt dihydrate, with an optical purity [HPLC] of 99.7% d(+).

Example 4

To a solution of 99.8 g (0.48 mol) ibuprofen [89% d(+)] in 150 g hexane was added 9.7 g NaOH (0.24 mol), and 4.3 g (0.24 mol) water. The contents were heated to 55° C. and held for 0.5 hour followed by cooling to 8° C. over 2 hours. Once the pot temperature reached 25° C., 24.5 g (0.24 mol) triethylamine was added over 0.3 hour. The product was isolated by vacuum filtration and washed with 2×100 g hexane. Overall product yield was 59.3 g (92.7% based on NaOH, 46.3% based on ibuprofen) with an optical purity of 99.3% d(+).

Example 5

To a solution of 100.1 g (0.48 mol) ibuprofen [89.6% d(+)] in 150 g hexane was added 9.7 g NaOH (0.24 mol) and 8.6 g water (0.48 mol). The contents were heated to 58° C. and held for 0.75 hour. The pot temperature was then cooled to 5° C. over 2 hours. As the pot temperature reached 25° C., 24.5 g (0.24 mol) triethylamine was added over 0.25 hour. The product was isolated by filtration, washed with 2×100 g hexane and air dried. The final product, 59.4 g (92.5% based on NaOH, 46.2% based on ibuprofen, sodium salt dihydrate (45.7 g, 61.0% on NaOH, 36.6% based on ibuprofen), had an optical purity of 98.8% d(+).

Example 6

To a solution of 100.3 g (0.48 mol) ibuprofen [89.5% d(+)] in 150 g hexane was added 2.45 g (0.024 mol) triethylamine, 11.6 g NaOH (0.29 mol) and 10.4 g water (0.58 mol). The contents were heated to 56° C. and held for 1 hour. The reaction mixture was then cooled to 5° C. over 2 hours; the product was isolated by vacuum filtration followed by washing with 2×100 g hexane. After air drying, 51.5 g of product is isolated (66.8% based on NaOH, 40.1% based on ibuprofen) with an optical purity of 99.3% d(+).

Example 7

To a solution of 100 g (0.48 mol) ibuprofen [89.4% d(+)] in 150 g hexane was added 11.65 g NaOH (0.29 mol), 10.45 g water (0.58 mol) and 4.9 g triethylamine (0.048 mol). The reaction mixture was heated to 56° C. and held for 1 hour, then cooled to 7° C. over 2 hours. The product was isolated by vacuum filtration followed by washing with 2×200 g hexane, and air dried to yield 59.17 g of product (77.0% based on NaOH, 45.2% based on ibuprofen) with an optical purity of 97.9% d(+).

Example 8

To a solution of 100.4 g (0.48 mol) ibuprofen [89.6% d(+)] in 150 g hexane was added 11.6 g NaOH (0.29 mol), 10.4 g water (0.58 mol) and 9.8 g triethylamine (0.097 mol). The reaction mixture was heated to 56° C. and held for 1 hour, then cooled to 5° C. over 2.5 hours. The product was isolated by vacuum filtration, washed with 2×125 g hexane, and air dried to yield 66.9 g of product (86.7% based on NaOH, 52.0% based on ibuprofen) with an optical purity of 96.2% d(+).

We claim:

1. A process for producing a substantially pure enantiomeric salt of an aryl-substituted aliphatic carboxylic acid having the formula:

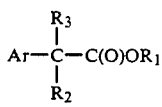

where $R_1$ is hydrogen or alkyl; $R_2$ and $R_3$ are different and are hydrogen, alkyl, cycloalkyl, phenyl, naphthyl, substituted phenyl, substituted naphthyl, haloalkyl, hydroxyalkyl, alkoxyalkyl, acyloxyalkyl, carboxyalkyl, alkoxycarbonylalkyl or cyanoalkyl and Ar is phenyl, naphthyl, substituted phenyl or substituted naphthyl; which comprises:
  i) reacting in an inert solvent an aryl-substituted aliphatic carboxylic acid enriched with one of its enantiomers with an inorganic base and a precipitation-enhancing amount of an organic base thereby forming a salt of said aryl-substituted aliphatic carboxylic acid enriched with said enantiomer, said organic base sufficient to enhance the precipitation of said salt, said salt having: a) at least one eutectic point; b) a composition that is not at the eutectic point; and c) a eutectic composition that is closer to the racemic composition of said salt than is the composition of said aryl-substituted carboxylic acid enriched with one of its enantiomers;
  ii) separating the salt of the substantially pure enantiomer of the aryl-substituted aliphatic carboxylic acid.

2. The process according to claim 1 wherein said inorganic base is a metal or ammonium hydroxide, carbonate, bicarbonate or chloride and the organic base is a low molecular weight amine selected from the group consisting of $C_1$ to $C_6$ linear or branched alkyl, $C_6$ to $C_{10}$ alkyl/$C_6$ to $C_{10}$ arylamines.

3. The process according to claim 2 wherein the metal is from Group IA or IIA of the Periodic Table of Elements and the organic base is a $C_1$ to $C_6$ linear or branched alkyl amine.

4. The process according to claim 3 wherein said inorganic base is sodium hydroxide and said organic base is triethylamine.

5. The process of claim 1 wherein the inert solvent for said reaction is a inert organic solvent.

6. The process according to claim 1 wherein the ratio of said organic base is from about 0.05 to about 0.95 mole per mole of aryl-substituted aliphatic carboxylic acid.

7. The process according to claim 6 wherein the ratio is from about 0.4 to about 0.6 made per mole of aryl-substituted aliphatic carboxylic acid.

8. The process of claim 1 wherein said aryl-substituted aliphatic carboxylic acid is treated with said organic base at a temperature of from about 0° C. to about 125° C.

9. The process according to claim 1 wherein $R_2$ is hydrogen, $R_3$ is methyl and $R_4$ is phenyl substituted with isobutyl.

10. A process for producing a substantially pure enantiomer of an aryl-substituted aliphatic carboxylic acid having the formula:

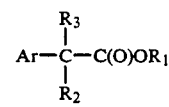

where $R_1$ is hydrogen or alkyl; $R_2$ and $R_3$ are different and are hydrogen alkyl, cycloalkyl, phenyl, naphthyl, substituted phenyl, substituted naphthyl, haloalkyl, hydroxyalkyl, alkoxyalkyl, acyloxyalkyl, carboxyalkyl, alkoxycarbonylalkyl or cyanoalkyl and Ar is phenyl, naphthyl, substituted phenyl or substituted naphthyl; which comprises:
  i) reacting in an inert solvent an aryl-substituted aliphatic carboxylic acid enriched with one of its enantiomers with an inorganic base and a precipitation-enhancing amount of an organic base thereby forming a salt of said aryl-substituted aliphatic carboxylic acid enriched with said enantiomer, said organic base sufficient to enhance the precipitation of said salt, said salt having: a) at least one eutectic point; b) a composition that is not at the eutectic point; and c) a eutectic composition that is closer to the racemic composition of said salt than is the composition of said aryl-substituted carboxylic acid enriched with one of its enantiomers;
  ii) separating the salt of the substantially pure enantiomer of the aryl-substituted aliphatic carboxylic acid;

iii) adding water to the reaction of step i) thereby forming a hydrated salt of said aryl-substituted aliphatic carboxylic acid enriched with one of its enantiomers; and iv) treating said hydrated salt to produce the substantially pure enantiomer of an aryl-substituted carboxylic acid.

11. The process of claim 10 wherein said aryl-substituted aliphatic carboxylic acid is 2-(4-isobutylphenyl)propionic acid.

* * * * *